United States Patent
Ashrafuzzaman

(10) Patent No.: US 10,916,330 B1
(45) Date of Patent: Feb. 9, 2021

(54) ENERGY-BASED METHOD FOR DRUG DESIGN

(71) Applicant: KING SAUD UNIVERSITY, Riyadh (SA)

(72) Inventor: Md. Ashrafuzzaman, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/892,614

(22) Filed: Jun. 4, 2020

(51) Int. Cl.
*C12N 15/115* (2010.01)
*G16B 5/20* (2019.01)

(52) U.S. Cl.
CPC ............ *G16B 5/20* (2019.02); *C12N 15/115* (2013.01); *C12N 2310/16* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 7,435,542 | B2 | 10/2008 | Shi et al. |
| 8,484,010 | B2 | 7/2013 | Tuszynski et al. |
| 2019/0042705 | A1 | 2/2019 | Zheng et al. |

OTHER PUBLICATIONS

Brooijmans et al, "Molecular Recognition and Docking Algorithms," Annual Review of Biophysics and Biomolecular Structure, 32(1), Jan. 28, 2003, 335-373.

Chushak et al., "In silico selection of RNA aptamers," Nucleic Acids Research, 37(12), e87, May 21, 2009.

Tseng et al., "Entropic Fragment-Based Approach to Aptamer Design," Chemical Biology & Drug Design, 78(1), Jul. 1-13, 2011.

Ashrafuzzaman et al., "A Computationally Designed DNA Aptamer Template with Specific Binding to Phosphatidylserine," Nucleic Acid Therapeutics, 23(6), 418-426, Dec. 2013.

Ashrafuzzaman et al., "Regulation of channel function due to physical energetic coupling with a lipid bilayer," Biochemical and biophysical research communications, 445(2), 463-468, Feb. 12, 2014.

Ashrafuzzaman, "Aptamers as Both Drugs and Drug-Carriers," BioMed Research International, . vol. 2014, 21 pages, Sep. 11, 2014.

Lombardo et al., "Soft Interaction in Liposome Nanocarriers for Therapeutic Drug Delivery," Nanomaterials, 6(7), 125, Jun. 25, 2016.

*Primary Examiner* — Sean McGarry

(74) *Attorney, Agent, or Firm* — Nath, Goldberg & Meyer; Richard C. Litman

(57) ABSTRACT

A method of designing aptamers includes building an aptamer by a seed-and-grow method optimizing screened coulomb interactions (SCI) and selecting aptamer length based on an aptamer target biological environment. Aptamers designed according to the method may comprise any DNA or RNA nucleotides. In particular, for example, aptamers may be designed according to the method to target lipids that may be found in membranes, such as liposomes or micelles. The lipids may be phosphatidylserine (PS) or phosphatidylcholine (PC).

9 Claims, 7 Drawing Sheets
Specification includes a Sequence Listing.

0th Order SCI Interaction Line ———
1st Order SCI Interaction Line ———
2nd Order SCI Interaction Line ▬▬▬
3rd Order SCI Interaction Line ▬▬▬

○ Effective Charge of Target
⊙ Effective Charge of A
● Effective Charge of G
◯ Effective Charge of T
⊕ Effective Charge of C

# ENERGY-BASED METHOD FOR DRUG DESIGN

INCORPORATION BY REFERENCE OF MATERIAL SUBMITTED IN COMPUTER READABLE FORM

The Applicants hereby incorporate by reference the sequence listing contained in the ASCII text file titled 33032_27_sequence_listing_ST25.txt, created May 5, 2020 and having 4 KB of data.

BACKGROUND

1. Field

The disclosure of the present patent application relates to a method of drug design, and particularly to a method of designing aptamer-based drugs based on optimal binding energies between the target and the aptamer and the biophysical environment of the target.

2. Description of the Related Art

Traditional aptamer discovery is mostly based on systematic evolution of ligands by exponential enrichment (SELEX) (Turek and Gold, 1990), where aptamer candidates are chosen from pools of candidates based on enrichment by binding with targets. Although target binding aptamers can be identified by SELEX (Turek and Gold, 1990; James, 2000; James, 2007; Hamula et al., 2006; Lao et al., 2009), this technology has disadvantages of requiring the design of extensive randomized DNA/RNA libraries a complex, costly and time intensive process of selecting candidates (Keefe et al., 2010). Further, SELEX cannot take into account in situ environment of targets.

U.S. Pat. No. 8,484,010 B2 to Tuszynski and Tseng, designs aptamers by a seed-and-grow approach, optimizing entropy of a target binding with aptamer fragments by an entropic fragment based approach (EFBA). EFBA is based on a process where a first seed residue is determined by optimizing entropy of the first seed selected from a small set of aptamer building blocks (ABB) bound to the target, and then adding an additional ABB, one at a time, while maximizing the entropy of target-aptamer complex with each addition. The EFBA does not account for binding energetics (minimum energy conformation) of the aptamer and target, particularly when the target is in a particular in situ environment such as making up or embedded in a liposome.

Thus, methods of designing aptamers useful for detecting a target, particularly in specific biological environments, such as embedded in a membrane, solving the aforementioned problems are desired.

SUMMARY

An embodiment of the present subject matter includes a method for designing aptamers, the method comprising steps of: creating a biophysical profile of a target (particularly a spatial charge distribution); selecting a set of possible aptamer building blocks from which to design the aptamer (i.e., DNA nucleotides, RNA nucleotides or a combination of both); selecting a first aptamer building block selected from the set of possible aptamer building blocks by calculating the zeroth order screened coulomb interaction term for each of the possible aptamer building blocks and selecting the possible aptamer building block corresponding to the maximal zeroth order screened coulomb interaction term to be the first aptamer building block; selecting a subsequent aptamer building block selected from the set of possible aptamer building blocks by calculating the subsequent order screened coulomb interaction term for each of the nucleotides and selecting the nucleotide corresponding to the maximal subsequent order screened coulomb interaction term; repeating the step of selecting a subsequent aptamer building block until the lowest subsequent order screened coulomb interaction term is less than an allowable minimal threshold (for example, less than or equal to zero) or until a predetermined length of n aptamer building blocks is reached; and designing the aptamer consists of the aptamer building blocks in the order selected. Other embodiments include methods of designing a variety of aptamers as above for various lengths in order to optimally bind a target in a membrane having a range of radii of curvature.

Aptamer lengths can be selected using theoretical technique considering lipid hosting target structure geometry, e.g., considering the geometry of liposomes. Numerical computation may help address the aptamer target binding energetics using appropriate in silico computing programs. Aptamers can be tested in vitro for their target binding strengths and statistical distribution around target binding sites. Positive in silico and in vitro target binding assays may rank and declare certain aptamers as therapeutic or diagnostic drugs. These aptamers may thus be used in treatments, e.g. to fight against various cancers, viral infections, etc.

These and other features of the present subject matter will become readily apparent upon further review of the following specification.

Figure 1A:
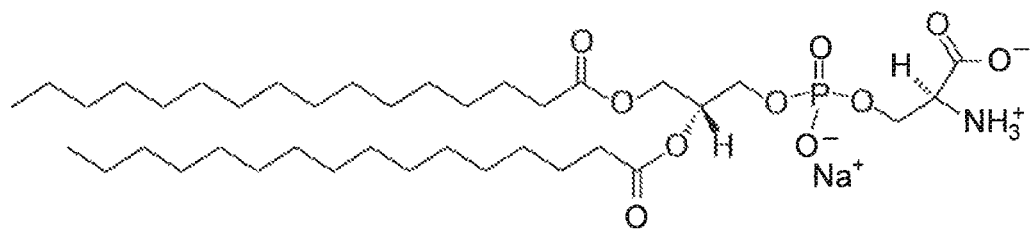
FIGS. 1A, 1B and 1C depict (1A) phosphatidylserine (PS) structure, (1B) phosphatidylcholine (PC) structure and (1C) potential aptamer building block (nucleotides) structure including charges and locations for the physical profile.

18), GGCGGCGGAG (PS/SCI) (SEQ ID NO: 1), CAAAAGGAGC (PC/SCI) (SEQ ID NO: 6).

Similar reference characters denote corresponding features consistently throughout the attached drawings.

DETAILED DESCRIPTION OF THE PREFERRED EMBODIMENTS

The present methods are directed to designing aptamers for detecting a target biomolecule based on charge-based interactions of each aptamer building block (ABB) or nucleotide and the target biomolecule. Optimal ABBs are associated with minimum binding energy conditions. When the aptamer approaches a target, the respective individual charges on each molecular site polarizes each other. As a result, the present methods account for interactions among many polarized charges in a two body (aptamer and target) system. The total energy in this two body coupling may be calculated as screened Coulomb interactions (SCIs) arising among many charge interactions. The resultant binding energy is the sum of energies resulting from interactions with various screening orders, as will be described below.

In embodiments of the present subject matter, aptamers may be designed from ABBs, and the ABBs may be, for example, DNA nucleotides, RNA nucleotides, or a combination thereof. One skilled in the art would understand that any other set of molecules may be used suitable for the ultimate application for any biological target molecule. In the following examples and discussion, DNA or RNA nucleotides are considered as aptamer building blocks (ABBs); i.e., DNA or RNA nucleotides, or in their combination, five nucleotides adenine, guanine, thymine, cytosine and uracil.

The aptamers can be theranostic (therapeutic and diagnostic) drugs to target biomolecules responsible for diseases. The biomolecules can be, for example, lipids, globular proteins, enzymes, specific amino acids, peptides, membrane proteins, DNA, and RNA. Lipids found in plasma membranes, liposomes, and viral envelopes can be responsible for various cellular diseases. In an embodiment, the biomolecules include lipids selected from the group consisting of phosphatidylcholine (PC) and phosphatidylserine (PS).

Screened Coulomb interactions (SCIs) can facilitate the aptamer design. SCIs arise among polarized charges in a drug target complex. These interactions underlie the drug target binding phenomena energetically. Thus, SCI can facilitate design of aptamers or general drugs from reverse use of information on the drug target binding energetics.

The aptamer can be designed such that the number and sequence of the ABBs minimize SCI binding energy. For example, a target lipid's nearest neighbor ABB is chosen to be that with minimum SCI binding energy, followed by subsequent ABBs, until subsequent aptamers add negligible SCI binding energy. In other embodiments, a set of SCI optimized aptamers of predetermined lengths (in numbers of ABBs, n) are determined for a target according to optimized SCI binding energy, and an aptamer is selected by length based on an expected or known in situ environment of the target, where the in situ environment is a membrane, i.e., the target comprises a membrane such as, for example a liposome.

An exemplary sets of aptamers for two lipid targets phosphatidylserine (PS) and phosphatidylcholine (PC) are set forth herein (Tables 6-14). PS and PC are two major lipid membrane components with implications in many cellular processes, and particularly incorporate into liposomes in model in vitro conditions, and in vivo. By an exemplary embodiment of the present specification, a liposome size specific optimal length of aptamers to target specific liposome membrane lipids may be determined. A few optimal aptamers were selected from a plurality of designed aptamers (Tables 6-14) and tested for binding by in vitro liposome binding assays. Positive binding was observed. It was also determined that the physiological condition of the buffer in which in vitro binding assays are performed also regulates the aptamer-liposome binding mechanisms.

Computer modelling of physical laws applied on a system or process can perform computational simulations which produces almost valid in-system data. As described herein, the computer program Mathematica 9.1 (Wolfram), was used to address in silico the PS or PC binding of nucleic acid nucleotides adenine (A), guanine (G), thymine (T), cytosine (C), and uracil (U) or nucleic acid aptamers. Aptamers were constructed from 4 nucleotides (A, G, T, C) of deoxyribonucleic acid (DNA) or 4 nucleotides (A, G, U, C) of ribonucleic acid (RNA) or 5 nucleotides combining both DNA and RNA nucleotides. The nucleotides are referred to herein as aptamer building blocks (ABBs). Theoretical formalism on body/charge interactions whereby charges interact in the presence of other charges through Screened Coulomb Interactions (SCIs) (Ashrafuzzaman and Tuszynslki, 2012) were considered in the calculations.

These and other features of embodiments of the present subject matter will be further explained and demonstrated by the following examples:

Example 1

Explanation of Screened Coulomb Interactions (SCI) and Calculations

Both target and ABB or aptamer, referred to generically herein as drug, were considered to consist of charges that interact among themselves when the drug approaches the target. The drug-target complex is a physical many-charge interaction system in a biological environment. In such systems, each charge may be described as interacting with another one according to SCI potential Vsc(k), as described in Ashrafuzzaman and Tuszynslki, 2012, where Vsc(k) may be described according to equation (1):

$$Vsc(k) = \frac{V(k)}{1 + \left(\frac{1}{2\pi k_B T}n\right)V(k)} \quad (1)$$

V(k) is the Coulomb interaction (CI) between two charges $q_i$ and $q_j$, and follows the relation of equation (2):

$$V(k) = (1/\varepsilon_0 \varepsilon_r) q_i q_j / k^2 \quad (2),$$

$k_B$ is the Boltzmann's constant, n is number density charges, k is wavenumber, T is absolute temperature representing the thermodynamic condition of the system, $\varepsilon_0$ is the dielectric constant in vacuum and $\varepsilon_r$ (~80 in aqueous water environment or ~2 in hydrophobic environment like membrane) is the relative dielectric constant of a media. Defining f(T,n) as $$f(T, n) = \frac{1}{2\pi k_B T} n \quad (3)$$

results in $$V_{sc}(k) = V(k)\left(\frac{1}{1+x}\right) \quad (4)$$

for $$x = \left(\frac{1}{2\pi k_B T} n\right) V(k) = f(T, n)V(k) \quad (5)$$

Taylor's series expansion results in:

$$\begin{aligned} V_{sc}(k) &= V(k)\left(\frac{1}{1+x}\right) \\ &= V(k)\left(1 + x + \frac{x^2}{2!} + \frac{x^3}{3!} + \ldots\right) \\ &= V(k)\left(1 + x + \frac{x^2}{2!} + \frac{x^3}{3!} + \ldots\right) \\ &= V(k) + V(k)x + V(k)\frac{x^2}{2!} + V(k)\frac{x^2}{3!} + \ldots \\ &= V(k) + V(k)x + V(k)\frac{x^2}{2!} + V(k)\frac{x^2}{3!} + \ldots \\ &= V(k) + V(k)f(T,n)V(k) + V(k)\frac{(f(T,n)V(k))^2}{2!} + \\ &\quad V(k)\frac{(f(T,n)V(k))^3}{3!} + \ldots \\ &= V(k) + f(T,n)V(k)V(k) + \\ &\quad \frac{(f(T,n))^2}{2} V(k)V(k)V(k) + \\ &\quad \frac{(f(T,n))^3}{6} V(k)V(k)V(k)V(k) + \ldots \end{aligned} \quad (6)$$

This may be otherwise written as, $$V_{sc}(k) = SCI^0 + SCI^1 + SCI^2 + SCI^3 + SCI^4 + \ldots \quad (7)$$

Here $SCI^i$ (i=0, 1, 2, 3, 4, ... etc.) represents the $i^{th}$ order SCI with i=0 representing the CI interaction.

The aptamer consists of multiple ABBs (at least n=2 ABBs). To illustrate how an aptamer may interact with a target molecule using SCI formalism, an exemplary aptamer-lipid interaction is described herein. Exemplary biologically and therapeutically relevant lipids include PS and PC and the aptamer can include nucleotide sequences specific for a target structure, for example, DNA sequence AGGGTT (telomere), AAAAAA, AAA, GGGGG, GGG, ATGCTT, etc.

In some embodiments, PS is the target. PS plays an important role in apoptosis.

Apoptosis is a biomolecular process of programmed cell death in which PS is externalized across a cell membrane. In normal cells (non-cancerous cells) PS exits across the cell membrane through an apoptotic region. In cancerous cells, apoptosis is stopped, and PS migration is distorted or stopped.

Many anticancer treatments rely on inducing apoptosis using certain therapeutic drugs. Induction of PS externalization in cancerous cells under treatment is a marker of a treatment's efficacy. A drug that binds to externalized PS may be used as a marker of anticancer drug efficacy. The PS binding drug may be used to quantify externalized PS and thus diagnose treatment stages. Such drugs will be defined herein as 'diagnostic drugs'. The scenario of an externalized PS in a lipid bilayer membrane will be used as an exemplary target for designing an aptamer according to the present method, said exemplary aptamer being a presumptive PS binding diagnostic drug.

Example 1.1

Aptamer-PS Interaction Energetics

Figure 1B:
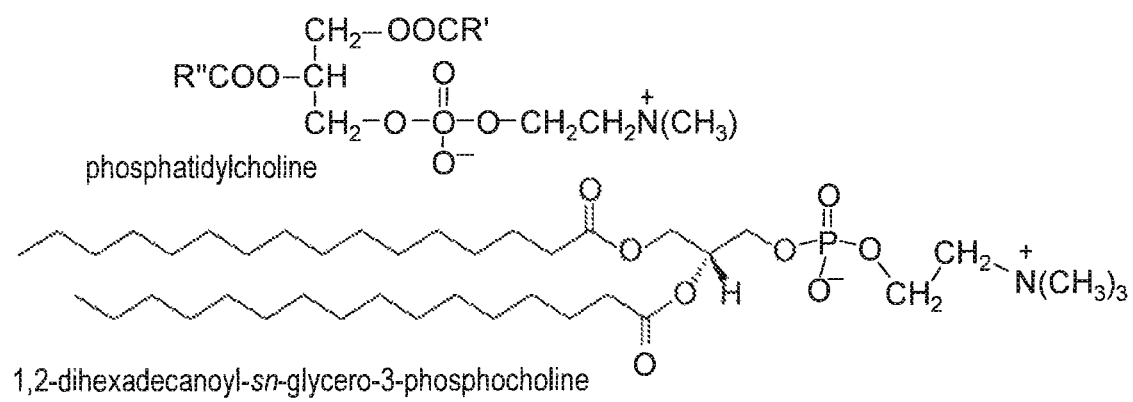
Figure 1C:
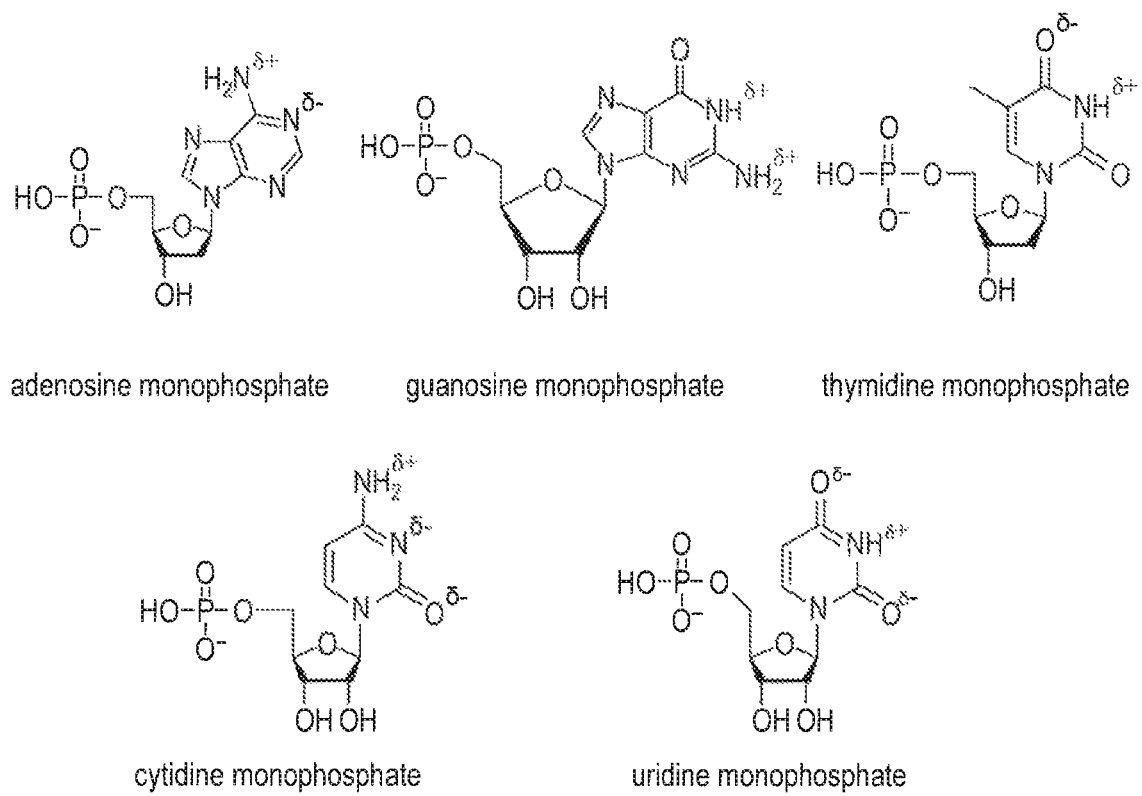

Exemplary calculation of SCI energetics for PS and will be presented for illustrative purposes. ABBs of only A are considered for simplicity. PS has a net negative charge, as it has two negative charges and one positive electron charge in solution, whereas PC has zero net charge, as it has one negative and one positive electron charges in solution) (see FIG. 1A). FIG. 1C shows DNA nucleotide ABBs A, T, G, C with charges as would be present in solution. A and T have 3 charges each, whereas G and C have 4 charges each, in aqueous solution.

When PS and one of A, T, G or C approach each other in solution, their charges interact. When a sequence of nucleotides, i.e., an aptamer, approaches PS, the many charges on the constituent nucleotides interact with those of PS. In a PS-AAAAA interaction, PS and each A are assumed to have an effective charge, namely $q_{PS}$ for PS and $q_A$ for A. The interaction system is modeled as a line of charges, for example.

The interaction energy is simply the coulomb interaction energy for the target and a single ABB (i.e., the first considered, or "seed", ABB), and may be calculated following the standard Coulomb formula. To calculate the SCI for higher order interactions (subsequent ABBs) following SCI formalism, a Fourier transformation is first performed on the respective higher order SCI terms, as:

$$V_{sc}(r) = \int d^3 k e^{(ik \cdot r)} V_{sc}(k) \quad (8)$$

Substituting equations (6) and (7) for $V_{sc}(k)$ into equation (8) and perform numerical computations (NCs), for example using software such as Mathematica 9.1 (according to details found in Ashrafuzzaman and Tuszynski, 2012) results in the $i^{th}$ order SCI ($SCI^i$) energy $E_i$, i=0, 1, 2, 3, ... m−1; m being the number of ABBs in the considered aptamer. The total PS-aptamer energy E is $$E = \sum_{i=0}^{m-1} E_i + \frac{1}{2} \sum_{i,j(i \neq j)=0}^{m-1} E_{i,j} \quad (9)$$

where $E_{i,j}$ is the inter-ABB SCI energy, whose derivation follows the identical SCI calculations as applied for $E_i$, explained above.

Example 1.2

SCI Optimization for Aptamer Design

The value of $E_i$ is specific for an ABB at $i^{th}$ position of an aptamer, the ABB having 4 possibilities for DNA or RNA, 5 for a combination: A, G, T (DNA)/U (for RNA), and C. There will be 4 or 5 values of $E_i$s in for aptamers built from ABBs selected from DNA or RNA, or a combination thereof, respectively, for any given value of i. The ABB corresponding to the lowest value of $E_i$ will be chosen for the $i^{th}$ position in the aptamer, as it minimizes SCI binding energy at $i^{th}$ position. The ABBs for any value of i may thus be chosen while designing aptamers. In the case where multiple ABBs contribute the same SCI energy value, any such optimizing ABB may be considered.

In an embodiment, the target is PS and ABBs are chosen among DNA nucleotides, exclusively. For illustrative purposes, PS and a nucleotide are considered to have just one effective charge each. $SCI^0$ binding energy ($E_{PS-ABB,SCI}^{0}$) may be calculated for ABB=A/G/T/C, giving 4 binding energy values corresponding to the 4 choices of ABBs. As an illustrative example, it is assumed that $E_{PS-A,SCI}^{0}$ is found to be the lowest in energy scale and A will be chosen as the first ABB.

The second ABB will be chosen by calculating $E_{PS-A,SCI}^{1}$, $E_{PS-G,SCI}^{1}$, $E_{PS-T,SCI}^{1}$ and $E_{PS-C,SCI}^{1}$. If, for example, $E_{PS-C,SCI}^{1}$ is the lowest energy, C will be chosen as the second ABB, i.e., the ABB at i=1. In other words, PS-A-C is presumably the most energetically stable considering up to $1^{st}$ order SCI, altogether accounting for $1^{st}$ and $2^{nd}$ positions in the nucleotide sequence.

This procedure may be repeated to add further nucleotides in the sequence by filling $3^{rd}$, $4^{th}$, $5^{th}$, etc. positions until the $E_{PS-ABB,SCI}^{i}$ contributes no or positive energy to the binding energy, corresponding to energetic saturation or beyond energetically unfavorable conditions. The aptamer length and ABB sequences can thus be chosen for a target alone.

Figure 2A:
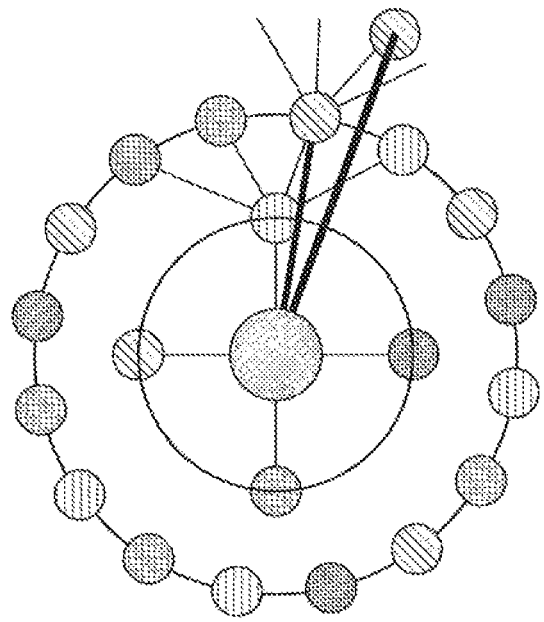
FIGS. 2A and 2B depicts a shell model of aptamer-target interactions (two-dimensional circle represents a spherical virtual shell). Increasing interaction line thickness represents increasing SCI order. Circular lines (FIG. 2A) represent the possible uniform geometric locations where ABBs (FIG. 2B) may be distributed.
Figure 2B:
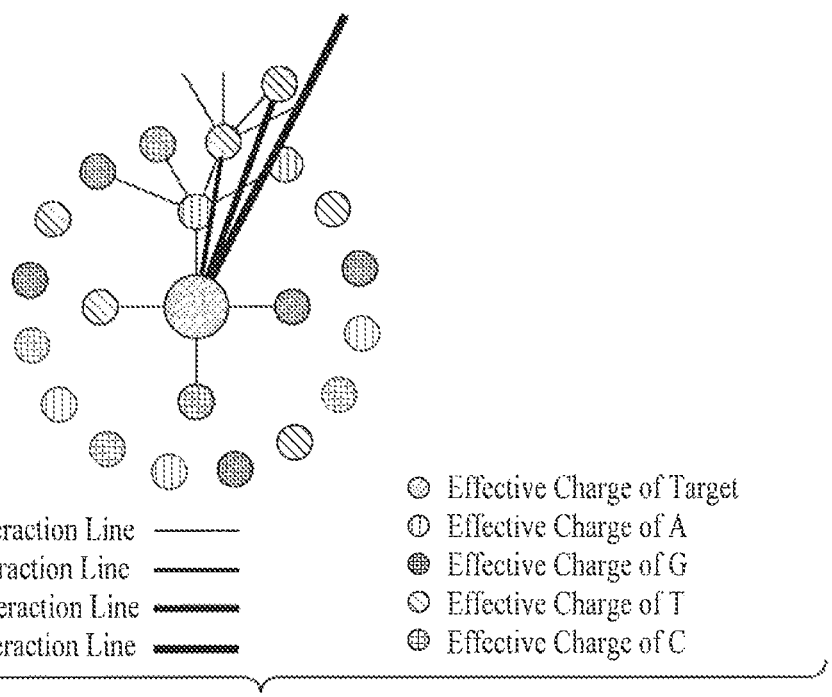

FIGS. 2A and 2B schematize the possible aptamers of different lengths and the contributions of SCI orders to the total SCI binding energy of the target-aptamer complex. In the particular example of ABBs selected from DNA nucleotides, for m DNA nucleotides in the sequence of an aptamer, there will $4^m$ possible aptamers. Specific inter-molecular bond distances may be considered specific to each ABB-ABB and target ABB bond.

A matrix of ABBs for a specific target can be created from the combinatorial arrangements illustrated in FIGS. 2A-2B. Considering 4 possible ABBs for the case of DNA nucleotides, for example, there are $4^m$ possible positions representing combinations, where m=1, 2, 3, . . . , $m_{max}$. The determination of $m_{max}$ is determined in view of the value of ABB-target SCI energy $E_i$ (see equations 8 and 9) does not change between $i=m_{max}-2$ and $i=m_{max}-1$ (saturation of binding energy condition). This $4^m$ represents the number of possible aptamers for a target with each having m number of ABBs. For DNA or RNA aptamers, $1 < m \leq m_{max}$ because aptamers require at least 2 ABBs.

Example 2

Exemplary Numerical Computation for Calculation of $E_i$

In general, for any single target structure if we consider k number of DBBs, we find that in each shell there are $k^m$ possible positions, accounting for the number drugs. The total number of drugs ($N_{drug}$), $$N_{drug} = \sum_{m=1}^{m_{max}} k^m \quad (10)$$

But in case of aptamers, as explained earlier, we require minimum 2 DBBs, so the total number of aptamers ($N_{apt}$), $$N_{apt} = \sum_{m=2}^{m_{max}} k^m \quad (11)$$

For DNA or RNA aptamers, k=4 (equation 11), but for their (DNA and RNA) combinations, k=5.

In this combinatorial DBB arrangements we find a lot of repeating sequences (considering forward and reverse sequences) which need to be excluded. E.g., AAG and GAA may be counted once. Thus the actual number of candidate drugs or aptamers will be lower than $N_{drug}$ or $N_{apt}$.

To perform numerical computation (NC) using Mathematica 9.1 (Ashrafuzzaman and Tuszynski, 2012) requires knowledge of charge distribution of target, in these examples either PS or PC, and ABBs, again in these examples A, G, T or U and C. FIGS. 1A-C show the positions and types of charges of the exemplary target and ABBs. The quantified charge distributions are presented in Tables 1 and 2.

TABLE 1

Amount of charged residues and induceable δ+ and δ− charges in ABBs (Lind et al., 2006).

| Amount of charge in base | δ+ (number) | δ− (number) | − (electron charge) |
|---|---|---|---|
| Adenine | 1 | 1 | 1 |
| Thymine | 1 | 1 | 1 |
| Cytosine | 1 | 2 | 1 |
| guanine | 2 | 1 | 1 |
| Uracil | 1 | 1 | 1 |

TABLE 2

Net charge amount and charge site in PS, PC and nucleotides

| substances | Charge | Net charge amount | Charge side |
|---|---|---|---|
| PS | Negative (−) | −e | $Po_4^-$, $NH_3^+$, $co_2^-$ |
| PC | Zwitterion | neutral | $Po_4^-$, $N^+ (CH_3)_3$ |
| A | Negative (−) | −e | $Po_4^-$, N δ−, H δ+ |
| T | Negative (−) | −e | $Po_4^-$, O δ−, H δ+ |
| C | Negative (−) | −e, −δe | $Po_4^-$, O δ−, N δ−, H δ+ |
| G | Negative (−) | −e, δe | $Po_4^-$, O δ−, H δ+, H δ+ |
| U | Negative (−) | −e | $Po_4^-$, O δ−, H δ+ |

Example 2.1

Numerical Computation on PS-Aptamer Binding Energy $E_{PS,i}$ and Selection of ABBs As an aptamer approaches to a PS, the individual ABBs may be considered having a net charges, as above, with target PS also has a net charge −1. Let us consider that the binding energy of an aptamer with PS in a potential well is $E_{PS,i}$, i=0, 1, 2, 3, . . . m−1; m being the number of ABBs in an aptamer (see equations 8 and 9, here $E_i$ is replaced with $E_{PS,i}$ to represent the energy as PS specific). The calculation of $E_{PS,i}$ follows SCI formalism, and is related to the calculation of free energy of association ($\Delta G_{I,II}$), where I and II represent two states, namely 'free' and 'bound' states, where $E_{PS,i} \approx \Delta G_{I,II}$ is calculated using NC as explained in Ashrafuzzaman and Tuszynski, 2012. Transitions between states I and II repeat at various values of r (x-axis coordinate). The energy difference between states I and II, $E_{PS,i}^{I} - E_{PS,i}^{II}$, is the free energy of association/dissociation $\Delta G_{PS,i}^{I \leftrightarrow II}$ where $I \leftrightarrow II$ indicates transitions through association/dissociation. Table 3 summarizes the NC computed logarithmic values of $E_{PS,i}^{I}$ and $E_{PS,i}^{II}$ for i=1, 2, ... 9. Table 4 present the NC computed logarithmic values of $E_{PS,i}$ at i=0 for PS-A where $E_{PS,0}^{I}$ and $E_{PS,0}^{II}$ are given for SCI orders 1, 2, 3, 4 and 5.

In a PS-aptamer interaction, inter particle (PS and any ABB, and between ABBs) average distance is assumed to be equal to the PS head group diameter ~7.5 Å. High and Low represent energy states I and II with logarithmic values of $E_{PS,i}^{I}$ and $E_{PS,i}^{II}$, respectively. As all state II values are as negligible as shown in SCI order 1 (see Table 3), the other state II values (low) are not shown. 9 SCI orders, $1 \leq i \leq 9$ are shown in Table 3, where the product of charges for all values of i is $\delta e^2$, with a small fraction $\delta = 0.1$ being estimated as the typical amount of induced charge while performing computation. Identical assumptions are applied for PC-aptamer binding energy calculations.

TABLE 3

Binding energy of DNA and RNA ABBs with PS (table 3A) and PC (table 3B) for different SCI orders. GGCGGCGGAG (SEQ ID NO: 1) is the optimized aptamer for PS, for example.

| Target-ABB | | CI, i = 0 | i = 1 Low | i = 1 High | i = 2 High | i = 3 High | i = 4 High | i = 5 High | i = 6 High | i = 7 High | i = 8 High | i = 9 High |
|---|---|---|---|---|---|---|---|---|---|---|---|---|
| PS | A | | 18.419 | 737.158 | 1377.51 | 1936.22 | 2504.57 | 3072.91 | 3213.72 | 4199.97 | 4204.35 | 4699.66 |
|  | G | | 18.373 | 737.112 | 1377.51 | 1727.65 | 2222.91 | 3072.91 | 3213.45 | 4199.97 | 4768.32 | 4699.25 |
|  | T | | 18.419 | 737.158 | 1377.51 | 1936.22 | 2504.57 | 3072.91 | 3213.72 | 4199.97 | 4204.35 | 4699.66 |
|  | C | | 18.4604 | 737.199 | 1232.55 | 1727.91 | 2223.26 | 2718.62 | 3213.97 | 4199.97 | 4768.32 | 4700.04 |
|  | U | | 18.419 | 737.158 | 1377.51 | 1936.22 | 2504.57 | 3072.91 | 3213.72 | 4199.97 | 4204.35 | 4699.66 |
| PC | A | | 17.419 | 736.158 | 1230.47 | 1724.78 | 2219.1 | 3063.28 | 3631.63 | 3702.04 | 4758.68 | 5317.39 |
|  | G | | 18.2763 | 809.169 | 1232.19 | 1727.36 | 2222.53 | 2717.7 | 3212.87 | 4199.97 | 4203.21 | 5327.03 |
|  | T | | 18.3275 | 737.066 | 1232.29 | 1936.22 | 2222.73 | 2717.95 | 3213.17 | 4199.97 | 4203.62 | 5327.03 |
|  | C | | 18.3732 | 737.112 | 1377.51 | 1727.65 | 2222.91 | 3072.91 | 3213.45 | 4199.97 | 4768.32 | 4699.25 |
|  | U | | 18.3275 | 737.066 | 1232.29 | 1936.22 | 2222.73 | 2717.95 | 3213.17 | 4199.97 | 4203.62 | 5327.03 |

TABLE 4

Direct interaction energy of ABB with PS and PC for the screening orders ($1 \leq i \leq 5$) in a direct PS-nucleotide complex considering the intra-charge distribution. The corresponding product of charges that were considered in NC are presented within first bracket with i. For partial charges in $3^{rd}$, $4^{th}$ and $5^{th}$ order reactions, $\delta e = 0.1e$ (see the charge distribution in table 5).

| | | i = 1 ($-e^2$) Low | i = 1 ($-e^2$) High | i = 2 ($e^2$) High | i = 3 ($\delta e^2$) High | i = 4 ($-\delta e^2/\delta e^2$) High | i = 5 ($-\delta e^2$) High |
|---|---|---|---|---|---|---|---|
| Energy | Direct | | | | | | |
| PS | A | 4.22 | 799.53 | 1348.61 | 1680.33 | 2158.59 | N/A |
|  | T | 4.22 | 799.53 | 1348.61 | 1680.33 | 2158.59 | N/A |
|  | C | 4.38 | 799.53 | 1348.61 | 1679.99 | 2437.14 | 2986.22 |
|  | G | 4.38 | 723.74 | 1348.61 | 1680 | 2437.14 | 2636.25 |
|  | U | 4.22 | 799.53 | 1348.61 | 1680.33 | 2158.59 | N/A |

| | | i = 1 ($e^2$) Low | i = 1 ($e^2$) High | i = 2 ($\delta e^2$) High | i = 3 ($-\delta e^2/\delta e^2$) High | i = 4 ($-\delta e2$) High | i = 5 |
|---|---|---|---|---|---|---|---|
| Energy | Direct | | | | | | |
| PC | A | 4.21296 | 799.536 | 1348.61 | 1897.69 | N/A | |
|  | T | 4.21296 | 799.536 | 1348.61 | 1897.69 | N/A | |
|  | C | 7.56063 | 723.806 | 1348.61 | 1680.28 | 2158.52 | |
|  | G | 3.56063 | 723.806 | 1348.61 | 1680.28 | 2158.52 | |
|  | U | 4.21296 | 799.536 | 1348.61 | 1897.69 | N/A | |

Distribution of charges in direct PS-ABB pairs (see the charges
in FIG. 1). PS represents the left-most 3 charges, the next two
entries are contributed by nucleotides A, T, C, G, U (top to bottom).
Charges in a PS-ABB pair are assumed to be evenly distributed over
a length of (7.5 + 3.3) Å. Left most charge interacts with $1^{st}$, $2^{nd}$,
$3^{rd}$, $4^{th}$ and $5^{th}$ order SCI with the rest of the charges.
Similar calculations can be performed for PC.

| | | | | | |
|---|---|---|---|---|---|
| −e | +e | −e | −δe | | +δe |
| −e | +e | −e | −δe | | +δe |
| −e | +e | −e | −δe | −δe | +δe |
| −e | +e | −e | −δe | +δe | −δe |
| −e | +e | −e | −δe | | +δe |

For each value of i, $E_{PS,i}$ has 4 alternate values corresponding to 4 different options of nucleotides or ABBs of DNA or RNA. The lowest value of $E_{PS,i}$ accounts for the type of ABBs in the sequence. If more ABBs account for identical lowest energy value the choice of ABB type selection for any specific position is more than one. The multiple options for ABBs at various values of i account for increased number of aptamers. The total number of possible aptamers $N_{apt}$ (referred to as $N_{PS,apt}$ for PS) depends on the value of $m_{max}$ as discussed previously. The optimal length ($l_{opt}$) of an aptamer corresponds to the value of $m_{max}$, beyond which the addition of ABBs contributes negligible or destabilizing binding energy. According to the present method, the optimized aptamer for free target would be around a length $l_{opt}$. The value of $l_{opt}$ may be different based on the geometry and structure of a region where the target molecule, e.g., PS or PC, is situated, i.e., its in situ environment. The target region may be, for example, a planar lipid bilayer or a liposome, in which lipids organize themselves to form a structure having a specific curvature profile, and the target comprises the structure.

Example 3

Below are aptamers that were discovered using the exemplary methods to target PS and PC. These aptamers are designed to demonstrate the method's suitability to design aptamers using these two target molecules as examples. Numerical computations for deriving the aptamers theoretically are provided in J. Comp. Theor. Nanoscience. The same technique may be used to design aptamers for any target given a charge distribution thereof.

Example 3.1

PS Aptamers

TABLE 6

PS aptamers from combination of DNA
and RNA nucleotides. Aptamers with
various sequences are selected for fixed
aptamer length is fixed with only 10 ABBs.
Relaxing energy condition starting from
rightmost ABB and continue leftward gives
ranked aptamers. G, the left most ABB comes
from choosing the lowest $1^{st}$ order SCI energy in
direct PS-nucleotide interaction (see table 4).
Only the 4 top PS binding aptamers are presented.

| PS aptamers | Best to worst: 1,2,3,4 (1 is the best) |
|---|---|
| GGCGGCGGAG (SEQ ID NO: 1) | 1 ($8^{th}$ ABB from left and onward ones account for varied energetics in their PS binding) |
| GGCGGCGGTG (SEQ ID NO: 2) | 2 |
| GGCGGCGGUG (SEQ ID NO: 3) | 3 |
| GGCGGCGAAG (SEQ ID NO: 4) | 4 |

Best aptamer sequence relies on lowest energy conformation (see tables 3 and 4). Consequently, $2^{nd}$ to the best aptamer sequences have the lowest energy conformation except at the $9^{th}$ order, sequence in the $9^{th}$ order has changed by $2^{nd}$ lowest energy conformation and $3^{rd}$ best aptamer sequence relies on lowest energy conformation except at $8^{th}$ order, sequence in the $8^{th}$ order has changed by $2^{nd}$ lowest energy-conformation. Finally $4^{th}$ best aptamer sequence relies on lowest energy conformation except at $8^{th}$ order and $9^{th}$ order, sequences in the $8^{th}$ and $9^{th}$ order have changed by $2^{nd}$ lowest energy conformation. Further leftward progression in searching for lowest energy conformation ensures in general the discovery of many aptamer sequences within same length.

Identical analogy is applied to discover PS aptamers from DNA nucleotides A, G, T, C (see table 7) and RNA nucleotides A, G, U, C (see table 8).

TABLE 7

PS aptamers from DNA nucleotides.

| PS aptamers | Best to worst: 1,2,3,4 |
|---|---|
| GGCGGCGGAG (SEQ ID NO: 1) | 1 |
| GGCGGCGGAA (SEQ ID NO: 5) | 2 |
| GGCGGCGGTG (SEQ ID NO: 2) | 3 |
| GGCGGCGAAG (SEQ ID NO: 4) | 4 |

TABLE 8

PS aptamers from RNA nucleotides.

| PS aptamers | Best to worst: 1,2,3,4 |
|---|---|
| GGCGGCGGAG (SEQ ID NO: 1) | 1 |
| GGCGGCGGAA (SEQ ID NO: 5) | 2 |
| GGCGGCGGUG (SEQ ID NO: 3) | 3 |
| GGCGGCGAAG (SEQ ID NO: 4) | 4 |

Example 3.2

PC Aptamers

The following tables provide SCI optimized PC targeted aptamers of various pre-defined lengths. Tables 9 (fixed length aptamers) and 10 (varying length aptamers) present sets of PC aptamers from both combination of both DNA and RNA nucleotides. Tables 11 (fixed length aptamers) and 12 (varying length aptamers) present sets of PC aptamers from DNA nucleotides. Tables 13 (fixed length aptamers) and 14 (varying length aptamers) present sets of PC aptamers from RNA nucleotides.

TABLE 9

PC aptamers from combination of DNA and RNA nucleotides (following identical analogy like that of PS, table 6). C or G at left most position are chosen due to their identical energetic presence at $1^{st}$ order SCI energy in direct PS-nucleotide interaction (see table 4B). Only a few aptamers are presented here to demonstrate the design strategy.

| PC aptamers | Best to worst: 1,2,3,4 |
|---|---|
| CAAAAGGAGC (SEQ ID NO: 6) | 1 |
| GAAAAGGAGC (SEQ ID NO: 7) | |
| CAAAAGGAGA (SEQ ID NO: 8) | 2 |
| GAAAAGGAGA (SEQ ID NO: 9) | |
| CAAAAGGATC (SEQ ID NO: 10) | 3 |
| GAAAAGGATC (SEQ ID NO: 11) | |
| CAAAAGGAUC (SEQ ID NO: 12) | |
| GAAAAGGAUC (SEQ ID NO: 13) | |
| CAAAAGGATA (SEQ ID NO: 14) | 4 |
| GAAAAGGATA (SEQ ID NO: 15) | |
| CAAAAGGAUA (SEQ ID NO: 16) | |
| GAAAAGGAUA (SEQ ID NO: 17) | |

TABLE 10

PC aptamers while aptamer length progresses by selecting energetically most stable ABBs. Relaxed energy condition starting from leftmost ABB and continuing in a rightward progression.

| PC aptamers | Best to worst: 1,2 3,4. |
|---|---|
| CA | 1 |
| GA | |
| CT | 2 |
| GT | |
| CU | |
| GU | |
| CAA | 1 |
| GAA | |
| CAG | 2 |
| GAG | |
| CAAA | 1 |
| GAAA | |
| CAAG | 2 |
| GAAG | |
| CAAAA | 1 |
| GAAAA | |
| CAAAG | 2 |
| GAAAG | |
| CAAAAG | 1 |
| GAAAAG | |
| CAAAAT | 2 |
| GAAAAT | |
| CAAAAU | |
| GAAAAU | |

TABLE 11

PC aptamers from DNA nucleotides.

| PC aptamers | Best to worst: 1,2,3,4 |
|---|---|
| CAAAAGGAGC (SEQ ID NO: 6) | 1 |
| GAAAAGGAGC (SEQ ID NO: 7) | |
| CAAAAGGAGA (SEQ ID NO: 8) | 2 |
| GAAAAGGAGA (SEQ ID NO: 9) | |
| CAAAAGGATC (SEQ ID NO: 10) | 3 |
| GAAAAGGATC (SEQ ID NO: 11) | |
| CAAAAGGATA (SEQ ID NO: 14) | 4 |
| GAAAAGGATA (SEQ ID NO: 15) | |

TABLE 12

PC aptamers from DNA nucleotides, while aptamer length progresses by selecting energetically most stable ABBs.

| PC aptamers | Best to worst: 1,2,3,4 |
|---|---|
| CA | 1 |
| GA | |
| CT | 2 |
| GT | |
| CAA | 1 |
| GAA | |
| CAG | 2 |
| GAG | |
| CAAA | 1 |
| GAAA | |
| CAAG | 2 |
| GAAG | |
| CAAAA | 1 |
| GAAAA | |
| CAAAG | 2 |
| GAAAG | |
| CAAAAG | 1 |
| GAAAAG | |

TABLE 12-continued

PC aptamers from DNA nucleotides, while aptamer length progresses by selecting energetically most stable ABBs.

| PC aptamers | Best to worst: 1,2,3,4 |
|---|---|
| CAAAAT | 2 |
| GAAAAT | |

TABLE 13

PC aptamers from RNA nucleotides.

| PC aptamers | Best to worst: 1,2,3,4 |
|---|---|
| CAAAAGGAGC (SEQ ID NO: 6) | 1 |
| GAAAAGGAGC (SEQ ID NO: 7) | |
| CAAAAGGAGA (SEQ ID NO: 8) | 2 |
| GAAAAGGAGA (SEQ ID NO: 9) | |
| CAAAAGGAUC (SEQ ID NO: 12) | 3 |
| GAAAAGGAUC (SEQ ID NO: 13) | |
| CAAAAGGAUA (SEQ ID NO: 15) | 4 |
| GAAAAGGAUA (SEQ ID NO: 12) | |

TABLE 14

PC aptamers from RNA nucleotides, aptamer length progresses by selecting energetically most stable ABBs.

| PC aptamers | Best to worst: 1,2,3,4 |
|---|---|
| CA | 1 |
| GA | |
| CU | 2 |
| GU | |
| CAA | 1 |
| GAA | |
| CAG | 2 |
| GAG | |
| CAAA | 1 |
| GAAA | |
| CAAG | 2 |
| GAAG | |
| CAAAA | 1 |
| GAAAA | |
| CAAAG | 2 |
| GAAAG | |
| CAAAAG | 1 |
| GAAAAG | |
| CAAAAU | 2 |
| GAAAAU | |

Example 4

Selection of Aptamer Length for Target in Lipid Layer

Aptamer Length ($l_{Apt}$) depends on the geometry of the location where aptamers interact with target molecules. PS or PC as aptamer targets are typically found in either liposome or cell membrane lipid bilayers, in vivo. The following explains the development of a theoretical platform to determine optimal values for $l_{Apt}$. Once $l_{Apt}$ is known, a selection of aptamer candidates can be created around this length (plus or minus 1 ABB, for example).

In therapeutic applications, aptamers are designed to target specific lipids in cell membranes, liposomes or micelles having a size distribution. In general, liposomes are composed of a lipid bilayer separating an aqueous internal compartment from the bulk aqueous phase. Micelles are closed lipid monolayers with a fatty acid core and polar surface, or polar core with fatty acids on the surface (inverted micelle). Cells of prokaryotes (bacterial, archaea) and eukaryotes (protists, fungi, plants, animals) are typically between 1-5 µm and 10-100 µm, respectively. Cell membranes or plasma membranes (3-7 nm thick) surround cells, having a certain curvature at any given location. Liposomes may be classified by sizes as small unilamellar, large unilamellar, giant unilamellar and large multilamellar vesicles ranging in size between 20-100 nm, 100-400 nm, 1 µm and larger, 200 nm-3 µm, respectively. Liposomes are made out of the same types of materials, i.e., various lipids, as a cell membrane. In the following discussion, lipid bilayers are assumed as spherical shells with two monolayers comprising compositions of various lipids. Due to geometric constrain inner monolayer certainly contains fewer number of lipids than outer monolayer. For details, see Ashrafuzzaman, 2018 and Akbarzadeh et al., 2013, the contents of which are incorporated herein in their entirety. Micelle sizes ranges between 2-50 nm, depending on composition and concentration of materials therein. Micelles are small aggregates or composed of phospholipids, with hydrophilic head groups forming the outer shell.

For a target embedded in any lipid structure, a layer of a bilayer or monolayer, the lipid experiences the layer having a certain local curvature. For a very large curvature, such as a cell membrane, a single target molecule may experience effectively a planar membrane. Differences between a planar bilayer (equivalent to cell bilayer membrane) and what will be referred to as a liposome bilayer (having a curvature that is within a few orders of magnitude of the size of the target) lie include: stress induced energy per lipid molecule in a liposome's outer surface due to bending exists for a liposome bilayer, but is zero for a planar bilayer and due to the curvature of the liposome, surface residing lipids may occupy more surface area (in the hydrophilic region) per lipid than that of planar lipid bilayer. While determining aptamer lengths for aptamer-target in liposome interactions, these criteria are taken into account.

Example 4.1

Schematic Analysis on Aptamer Interaction with Planar Lipid Bilayer or Liposome

Figure 3A:
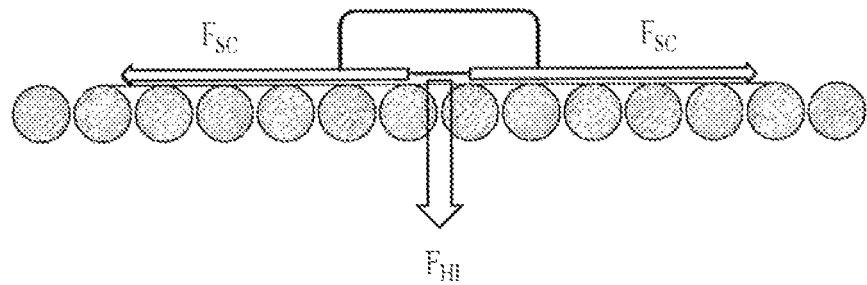
FIGS. 3A, 3B and 3C shows (3A) aptamer (red block) coupling with planar lipid monolayer (PLM); (3B) aptamer coupling with liposome surface or liposome lipid monolayer (LLM) has been schematized. $F_{SCI}$ and $F_{HI}$ are forces on the aptamer due to screened Coulomb interactions and hydrophobic interactions; (3C) shows curvature represented by radius r, while aptamer bending caused curvature with radius $r_{Apt}$.
Figure 3B:
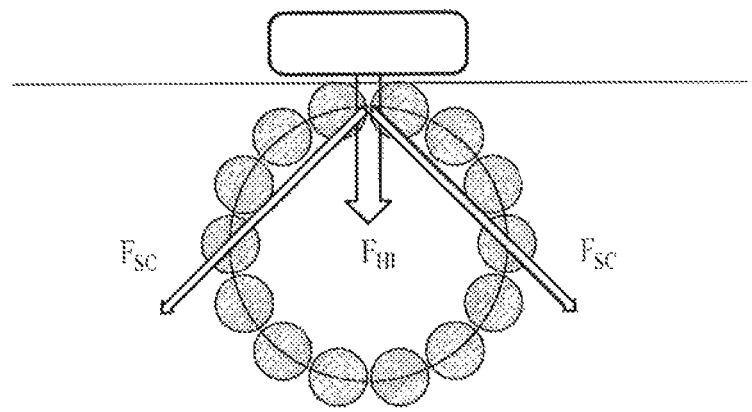

When an aptamer approaches a lipid membrane, it experiences interactions with the lipid membrane surface, i.e., a lipid monolayer. Beneath the lipid monolayer is hydrophobic core of the lipid bilayer. In cases of effectively planar bilayers and liposomes, the interaction driven coupling of aptamers with a target in the outer lipid monolayer of faces different geometrical constraints. See, e.g., FIGS. 3A-B. FIG. 3A shows an aptamer (blocks) coupling with a planar lipid monolayer (PLM), while FIG. 3B shows an aptamer coupling with liposome surface or liposome lipid monolayer (LLM). $F_{SCI}$ and $F_{HI}$ are forces acted on the aptamer by the host environment due to Screened Coulomb Interactions and hydrophobic interactions (HIs), respectively. The depicted 14 lipids across the PLM or LLM is arbitrary and for illustrative purposes, only. The surface binding interaction between aptamers with a target in a liposome outer layer are the same as for micelles, for the purposes of this analysis, but only liposome interactions will be explicitly discussed in the following.

In the case of aptamer-PLM coupling, the $F_{SCI}$ in opposite directions cancel each other and that leaves $F_{HI}$ to be the sole contributor in the binding energetics (see FIG. 3A, upper panel). But in the case of aptamer-LLM coupling $F_{SCI}$s act at an angle (ø) with the direction of $F_{HI}$ (see FIG. 3B). The value of ø changes spontaneously across the lipid layer. For simplicity of calculation ø may be considered on average constant for a short lipid chain over which the aptamer interactions extend.

4.2 Theoretical Analysis on Aptamer-Liposome Binding Energy Calculation

Total binding energy is $E_{tot,Apt}=E_{SCI}+E_{HI}$, where $E_{HI}$ is the hydrophobic binding energy due to hydrophobic pull $F_{HI}$ and $E_{SCI}$ is the total binding energy due to 2 $F_{SCI}$s.

$E_{tot,Apt}$ is found to be conformation specific and varies due to change of $E_{SCI}$ between liposome and planar lipid bilayer conformations. In terms of membrane pulling forces the analogy becomes clear.

Consider the total membrane pulling force of aptamer is $F_{tot,Apt}$.

For planar lipid layer (cell surface) conformation, ø=90°, $$F_{tot,Apt}=-F_{SCI}\cos 90°+F_{HI}+F_{SCI}\cos 90°=F_{HI}$$

For liposome conformation, 0°<ø<90°, $$F_{tot,Apt}=F_{SCI}\cos ø+F_{HI}+F_{SCI}\cos ø=F_{HI}+2F_{SCI}\cos ø$$

Figure 3C:
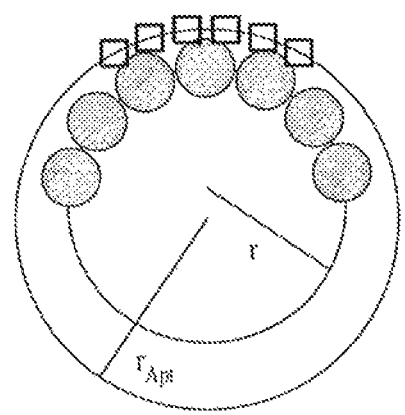

In general ø≥45° can be assumed for a special conformation when aptamer aligns across the liposome surface through no more than half of the circumference (πr), r being the liposome radius, see FIG. 3C. Here, the aptamer is a one dimensional (1D) chain of nucleotide bases, so while binding on the spherical surface of liposome aptamers bind across a circular region.

In above mentioned binding energy calculations, only the case when the liposome or membrane pulls aptamers towards its hydrophobic core is considered. This would be valid approximation in case when ø ↗ 90° (especially for binding of aptamers with planar lipid bilayer or extra-large liposome). Otherwise (especially for smaller liposome and micelle, ø<90°), there exists two other energy contributions provided by the bending conformations of both aptamers and lipid monolayer (liposome surface). Both of these energies take part in determining the total aptamer-liposome interaction energies.

Example 4.3

Strategy for Selection of $l_{Apt}$ Related to the Range of ø

While approaching a liposome, an aptamer experiences what can be approximated as a spherical half of the liposome. The other half can be considered as practically screened out. Therefore, ø falls within the range 45°≤ø≤90°. For the smallest liposome, ø approaches 45° whereas for the largest liposome, ø approaches 90°. For a cell, the surface is considered planar ø≈90°. Depending on the flexibility of the aptamer, the maximum aptamer length ($l_{max}$) can be between the following two possible lengths: half of the liposome circumference=πr for flexible aptamers that can bend to the curvature of the liposome or the planar projection of the circumference=2r for very stiff aptamers (see FIG. 3C, which shows a flexible aptamer, as is the case for single strand DNA or RNA based aptamers). The minimum aptamer length ($l_{min}$) can be any length greater than one ABB that makes a stable aptamer using the fewest possible number of ABBs.

Considering a distribution of liposomes with radii r between a smallest $r_S$ and largest $r_L$. The maximum number of ABBs in an aptamer may be at most $\pi r_L/a_{nu}$ or $2r_L/a_{nu}$, where $a_{nu}$ is the average distance covered by each ABB to construct an aptamer (see FIG. 3C). In principle, the aptamer can also curve back over itself on the three dimensional liposome hemisphere. It can also wrap around the sphere. In both cases, due to apparent rigidity, the aptamers may require excess amount of bending energies that may not be available from any kind of physical interactions with the target agents. This is why these possibilities have been excluded from the present calculations. In single strand DNA and RNA, $a_{nu}$≈0.33 nm. The maximum number of lipids that can interact by SCI with an aptamer in the smallest liposome is $\pi r_S/a_{lip}$ or $2r_A/a_{lip}$, where $a_{lip}$ is the average lipid head group diameter which is approximately 0.76 nm. For the purpose of calculations, it may be approximated that $a_{lip}≈2a_{nu}$, for DNA or RNA based aptamer-lipid interactions. $\pi r_S/a_{lip}=N_{min}$ is the minimum number of lipids expected to experience SCI for an aptamer binding with the liposome formed from the lipids. The larger the liposome, the more lipids will experience SCI with an aptamer, as in this case negligible aptamer bending would be required. The highest number of lipids experiencing SCI with an aptamer will be $\pi r_L/a_{lip}=N_{max}$, beyond which the interaction will be felt as if between an aptamer and an effectively planar lipid layer (i.e., a large spherical cell). In a case of aptamer-cell interactions, aptamers are assumed to be adsorbed on a two-dimensional cell surface. The aptamer on a cell surface fact interacts with (hypothetically) an infinite number of lipids along both directions of its length (although only a finite order of SCI terms will contribute non-negligibly to the energetics of the interaction).

For a liposome, define $2\pi r=N_{tot}\times a_{lip}$, where $N_{tot}$ is the total number of lipids across the circumference of spherical liposome. For example, in FIG. 3C, $N_{tot}$=14; the maximum possible aptamer length, $l_{max}=\pi r=7\times a_{lip}≈14a_{nu}$. In other words, in design the aptamer, it is not necessary to consider a nucleotide more than $N_{tot}*$, i.e., 14 nucleotides in the example of FIG. 3C, for binding with the specific sized liposome (FIG. 3C).

Example 4.5

Modeling Aptamer-Liposome Binding and Calculating Binding Energies

Entropic fragment based approach (EFBA) was previously used to designed a few PS binding DNA aptamers: AAAGAC being one of the best (strong target binding potency) PS binding aptamer short sequence (ASS), CAGAAAAAAAA (SEQ ID NO. 18) being one of the worst (poor target binding potency) PS binding aptamer long sequence (ALS) (Ashrafuzzaman and Tseng, 2016). Consistently, using SCI techniques described herein recovered identical length 6 ABB based optimal PS and PC binding ASS DNA aptamers GGCGGC and CAAAAG, respectively (see tables 7 and 11, respectively). Two SCI designed ALS DNA aptamers GGCGGCGGAG (SEQ ID NO: 1) and CAAAAGGAGC (SEQ ID NO: 6) for PS and PC, respectively (see tables 7 and 11, respectively) were chosen to compare their target binding potency with the EFBA designed ALS. See experimental binding results in FIG. 6.

$F_{SCI}$ may be calculated for 6 nucleotide aptamers, ASSs, for PS or PC. These aptamers will bind to 7 lipids (half of the arbitrarily chosen 14 lipids in FIG. 3C). When aptamers approach longitudinally may be considered as the initial aptamer adsorption process, but the ultimate adsorption state of the aptamer-liposome coupling will eventually be the aptamer adhering flush with the liposome, as in FIG. 3B-C. On average, the lipid could be considered to adhere to the middle of the aptamer, such that a lipid in the liposome may be approximated to on average interact with 3 nucleotides on both left and right sides. Total energy will be twice SCI energy of a lipid with 3 nucleotides in the sequence.

Example 4.6

Bending Energy

In the case of an aptamer binding with cell surface (planar lipid layer) there is no considerable bending in cell surface or aptamer structure. But in the case of liposome binding, the aptamers may experience bending towards the curved liposome surface. The liposome surface bending increases with the decrease of liposome size having smaller liposome diameter. In the case of aptamer-liposome interaction both aptamer and lipid monolayer under aptamer-liposome interaction region contain bending energies which can be considered as aptamer bending energy ($E_{B,Apt}$) and liposome bending energy ($E_{B,lip}$), respectively, and the corresponding bending forces are $F_{B,Apt}$ and $F_{B,lip}$, respectively. Bending energy works against liposome binding. The net aptamer-liposome binding energy ($E_{net,Apt}$) is, $$E_{net,Apt} = E_{tot,Apt} + E_{B,Apt} + E_{B,lip}$$

Bending force $F_{B,Apt}$ acting on aptamer follows Hooke's law for small deformation of length $\delta x$, $$F_{B,Apt} = -k_{Apt}\delta x$$

where $k_{Apt}$ is force constant active in nucleotide-nucleotide interaction energies in a single DNA strand (Ashrafuzzaman and Shafee, 2005).

Similarly, the lipid monolayer bending force $F_{B,lip}$ can be calculated using force constant $k_{lip}$ being calculated from lipid-lipid interaction energies. Bending force follows Hooke's law for small deformation, $$F_{B,lip} = -k_{lip}\delta x$$

The greater the bending, the larger the force opposing the aptamer binding. Smaller liposome require greater bending. But, due to smaller liposome diameter, the required $L_{max}$ is smaller, and thus the value of $\delta x$ is also smaller. The net liposome inward force on an aptamer ($F_{net,Apt}$) is, $$F_{net,Apt} = F_{tot,Apt} - F_{B,Apt} - F_{B,lip}$$

Aptamer bending energy can be approximated as DNA bending energy, which is proportional to both $1/r_{Apt}^2$ and the length of the aptamer $l_{Apt}$. Considering proportional constant $k = l_p k_B T$ (The persistence length $l_{P,Apt}$ for $l_p$ is a characteristic length scale for aptamer that relates the bending rigidity of the DNA chain to the thermal energy $k_B T$. The aptamer bending energy is $E = \frac{1}{2} k \cdot 1/r^2 = \frac{1}{2} l_{p,Apt} 1/r^2 k_B T$).

By the present model, $r_{Apt}$ is the radius of curvature of the aptamer due to aptamer bending (see FIG. 3C). Therefore, $$E_{B,Apt} = (1/2) k_{B,Apt} l_{Apt} / r_{Apt}^2 = (1/2)(l_{P,Apt} k_B T) l_{Apt} (1/r_{Apt/lip})^2)/r^2 = (k_B T/2)(1/r_{Apt/lip})^2) l_{P,Apt} l_{Apt} / r^2$$

where $r_{Apt} = r_{Apt/lip} r$ with usually $r_{Apt/lip} \geq 1$. r is the radius of the liposome, considered as the radius of spontaneous curvature caused by lipid monolayer bending.

The work of Bezrukov (Bezrukov et al., 1998) on the calculation of work of forcing one lipid molecule from the hexagonal $H_{II}$-phase into the lamellar phase finds the following expression:

$$E_{B,lip} = (1/2) a_{lip}^2 k_{B,lip} / r^2$$

where $k_{B,lip}$ is the monolayer bending modulus ($\sim 10\ k_B T$) and r, the radius of the liposome, is considered to be the radius of spontaneous curvature.

Therefore, using the value of the lipid bending modulus mentioned above is, $$E_{B,lip} = 5 k_B T\ a_{lip}^2 / r^2.$$

Example 4.7

Computing $E_{SCI}$ and Deducing Aptamer Lengths

Following theoretical and computational analysis presented in ref. (Ashrafuzzaman and Tuszynski, 2012):

$$E_{SCI} \sim \exp((1/\delta_{Apt/lip}) r)$$

where $\delta_{Apt,lip}$ is equivalent to correlation length, a parameter determining the line of interaction between aptamer and lipid monolayer. It is most likely a length within $2 a_{nu} \leq 2\delta_{Apt,lip} \leq L_{max}$ or, $a_{nu} \leq \delta_{Apt,lip} \leq L_{max}/2$. Considering that there is needed at least 2 nucleotides to qualify a nucleotide sequence as an aptamer. Therefore (Ashrafuzzaman and Tuszynski, 2012), $$E_{SCI} = [(1/\epsilon_0 \epsilon_r) q_{nu} q_{lip}]^s \exp((1/\delta_{Apt,lip}) r)$$

where s is screening order to be calculated based on number of nucleotides and lipids and vice versa under SCI interactions. $s = 1, 2, 3, \ldots$, etc. for $0^{th}$ (direct Coulomb interaction), $1^{st}, 2^{nd}, \ldots$, etc. order of screening in screened Coulomb interactions. The longer the aptamer the higher is the order of screening. $q_{nu}$ and $q_{lip}$ are effective charges on a nucleotide and a lipid headgroup, respectively. For simplicity, interactions between lipid tails are ignored.

In case of liposome adsorption of aptamers the resultant grand total/net energy of aptamer-liposome association is $$E_{net,Apt} = E_{tot,Apt} + E_{B,Apt} + E_{B,lip} = E_{HI} + [(1/\epsilon_0 \epsilon_r) q_{nu} q_{lip}]^s \exp((1/\delta_{Apt,lip}) r) + (k_B T/2)(1/r_{Apt/lip})^2 l_{P,Apt} l_{Apt}/r^2 + 5 k_B T\ a_{lip}^2/r^2$$

The net aptamer-liposome association force is $$F_{net,Apt} = -(d/dr) E_{net,Apt}$$

The optimal aptamer length will be determined at $r = r_0$ ($r_0$ being the optimal radius of liposome) for which $$F_{net,Apt}|_{r=r0} = -(d/dr) E_{net,Apt}|_{r=r0} = 0$$

$\delta_{Apt,lip} = n a_{nu}$, where $1 \leq n \leq r_L/a_{nu}$ (or, $1 \leq n \leq ((\pi r_L/2)/a_{nu})$). That means n is any number between 1 and a maximum value that gets determined by the size of the liposome, $r_L$ is considered here to be proportional to the radius of liposome that is under the interaction with aptamer. Regarding aptamer length:

$$l_{P,Apt} \approx l_{Apt} \approx 2\delta_{Apt,lip}.$$

$$a_{nu} = a_{lip}/2$$

and let us assume:

$r' = r/a_{lip}$.

The above equation for $E_{net,Apt}$ stands as:

$E_{net,Apt} - E_{HI} = [(1/\varepsilon_0\varepsilon_r)q_{nu}q_{lip}]^s \cdot 2 \cdot \exp(2r'/n) + (k_BT)\{(1/2)(1/r_{Apt/lip})^2\}l_{P,Apt}l_{Apt} + 5a_{lip}^2\}/r^2$ $= [(1/\varepsilon_0\varepsilon_r)q_{nu}q_{lip}]^s \cdot 2 \cdot \exp(2r'/n) + (k_BT)\{(1/2)(1/r_{Apt/lip})^2\}(n^2 a_{lip}^2 + 5a_{lip}^2)\}/r^2$ $= [(1/\varepsilon_0\varepsilon_r)q_{nu}q_{lip}]^s \cdot 2 \cdot \exp(2r'/n) + (k_BT)\{(1/2)(1/r_{Apt/lip})^2\}(n^2 + 5)\}/r'^2$ where n is a number that determines the number of nucleotides for constructing half of the aptamer length. No of nucleotide in the aptamer=2n. This means equal halves of the aptamer length experiencing SCI on both sides of the aptamer's contact/association region with the liposome. The order of screening is determined considering half of the length of the aptamer.

The above expression can now be rewritten as:

$\{(1/(K_BT))\}\{E_{net,Apt} - E_{HI}\} = \{[(1/\varepsilon_0\varepsilon_r)q_{nu}q_{lip}]^s/(k_BT)\}2\exp(2r'/n) + \{(1/2)(1/r_{Apt/lip})^2\}(n^2+5)\}/r'^2$.

$\{[(1/\varepsilon_0\varepsilon_r)Q_rq_{lip}^2]^s/(k_BT)\}2 \quad \exp(2r'/n) + \{(1/2)(1/r_{Apt/lip})^2\}(n^2+5)\}/r'^2$.

where $q_{nu} = Q_r q_{lip}$. $Q_r$ may be any value, e.g. $10^{-2}$, 1, 10, $10^2$, $10^3$, etc., in the case of zwitterionic lipids (Ashrafuzzaman and Tuszynski, 2012; 2012a). $K_BT \approx 1.38 \times 10^{-23}$ Joule/K (300 K). Thus, $\{(1/(K_BT))\}\{E_{net,Apt} - E_{HI}\}$ $= \{[(1/\varepsilon_0\varepsilon_r)Q_rq_{lip}^2]^s/(k_BT)\}2 \quad \exp(2r'/n) + \{(1/2)(1/r_{Apt/lip})^2\}(n^2+5)\}/r'^2$.

$Q_r^s\{[(q_{lip}^2/\varepsilon_0\varepsilon_r)]^s/(k_BT)\}2 \quad \exp(2r'/n) + \{(1/2)(1/r_{Apt/lip})^2\}(n^2+5)\}/r'^2$.

Figure 4:
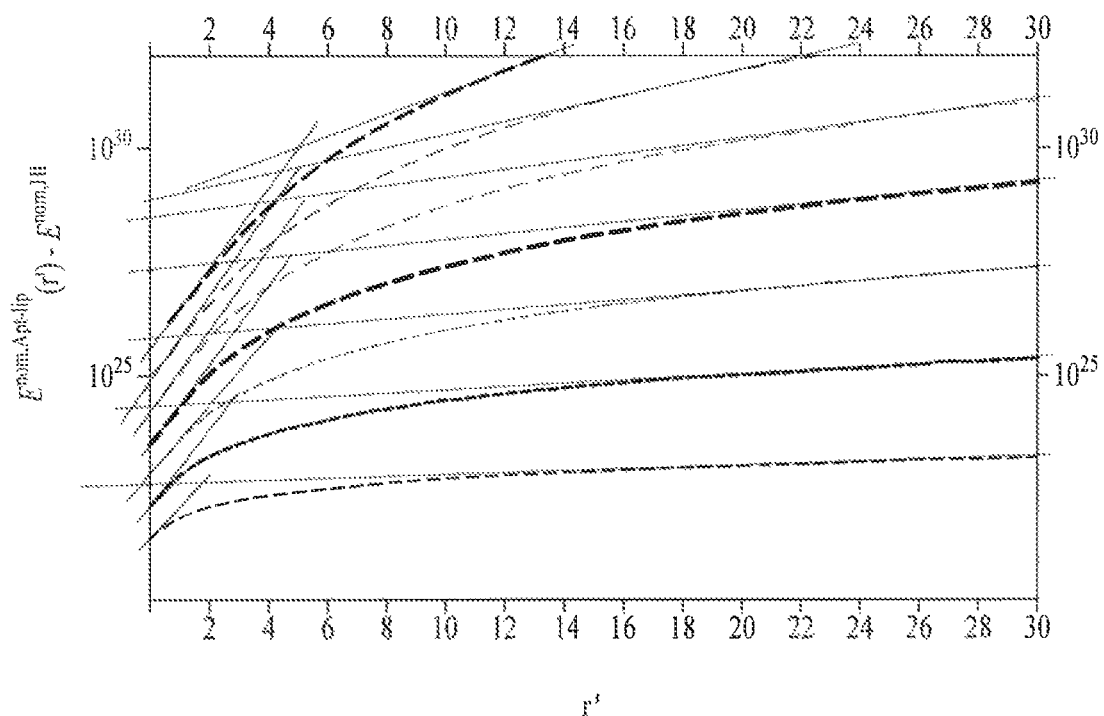
FIG. 4 shows plots resulting from exemplary calculations for length optimization given n=1 (aptamer length=2 nucleotides), $Q_r$=5. $r'_{cut-off}{}^1$=2.0, $r'_{cut-off}{}^2$=2.5, $r'_{cut-off}{}^3$=3.1, $r'_{cut-off}{}^4$=3.5, $r'_{cut-off}{}^5$=3.6, $r'_{cut-off}{}^6$=4.0, $r'_{cut-off}{}^7$=4.6. Here $r'=r/a_{lip}$. Tangent lines intersections indicate the cut-off radii $r'=r/a_{lip}$ of the typical membrane lipids

If the charge on the lipid is determined in light of the dielectric environment, $q_{lip}^2 \approx \varepsilon_0 \varepsilon_r$. Taking the lowest possible value of $r_{Apt/lip} \approx 1$ (valid for the case when aptamer is absolutely adsorbed by the liposome), and performing numerical computation using Mathematica 9.1 gives values for the above expression (left side in above equation) that can be plotted for various choices of $Q_r$ and n. FIG. 4 is one example, calculated for n=1 (aptamer length=2 nucleotides), $Q_r=5$. $r'_{cut-off}^1=2.0$, $r'_{cut-off}^2=2.5$, $r'_{cut-off}^3=3.1$, $r'_{cut-off}^4=3.5$, $r'_{cut-off}^5=3.6$, $r'_{cut-off}^6=4.0$, $r'_{cut-off}^7=4.6$, where $r'=r/a_{lip}$.

In other words, the energy can be plotted as a function of r and the corresponding cut-off values of r are as follows: $r_{cut-off}^1=0.5a_{lip}$, $r_{cut-off}^2=1.0a_{lip}$, $r_{cut-off}^3=2.0a_{lip}$, $r_{cut-off}^4=3a_{lip}$, $r_{cut-off}^5=3.5a_{lip}$, $r_{cut-off}^6=3.7a_{lip}$, $r_{cut-off}^7=4.0a_{lip}$, respectively. The value of any $r'_{cut-off}^s$ or $r_{cut-off}^s$ is assumed to be the value of r' or r corresponding to the meeting point of two slopes, as presented here. At meeting it is assumed that the value of the resultant force $F_{net,Apt}$ starts growing from the value 0 at $r=r_0$. Here the range of liposome size lies in values of r lying within approximately $2.0a_{lip}$–$5.0a_{lip}$ (see the meeting points of the slopes) while the screening order is considered to reach up to $7^{th}$ order. The cut-off values may be calculated in subsequent similarly for other chosen values of n and $Q_r$.

Figure 5:
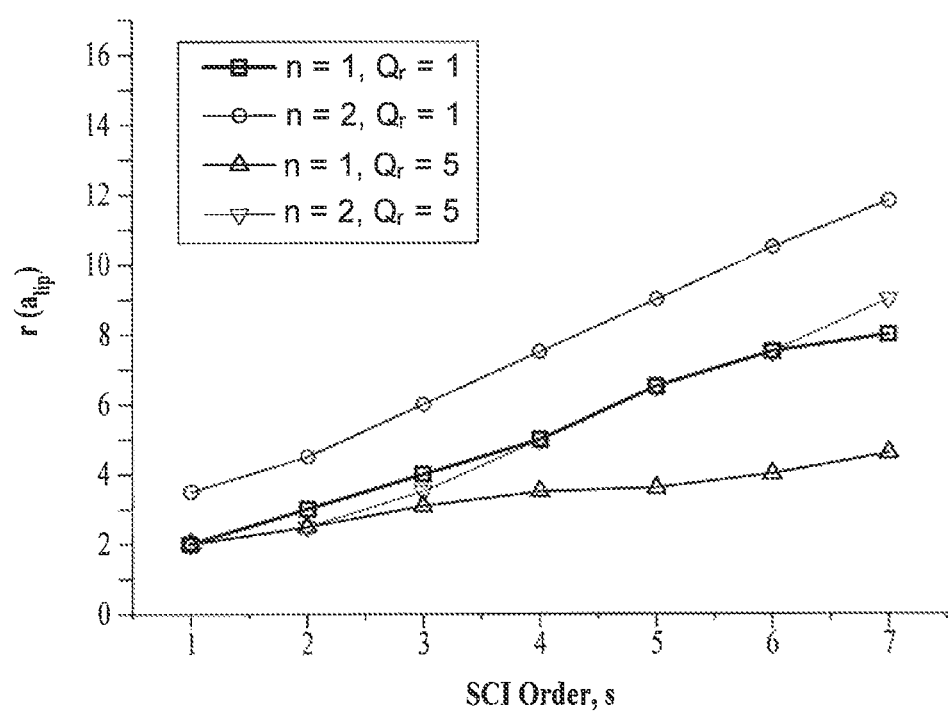
FIG. 5 shows a plot of liposome size r versus SCI screening order s, specific for aptamer length of 2n ABBs.

FIG. 5 shows a plot of liposome size versus SCI screening order s, specific for aptamer length consisting of 2n ABBs. A known value of r helps determine the maximum value of s from this plot. 5 increases with the increase of r. 5 suggests how many maximum number of ABBs are needed to be considered in determining the optimal aptamer's length. As nucleotide charge increases relative to the charge on lipid, the value of r is more fixed (see the bottom line, n=1, $Q_r=5$).

This graph (FIG. 5) is created based on values deducted from above graphs like FIG. 4 created using Mathematica 9.1.

Here aptamer length $l_{Apt} = 2na_{nu}$ where n=1, 2, 3, ..., $n_{max}$. Here $n_{max}$ is any higher order number to be determined considering the size of the liposome and such that the maximum possible aptamer length $L_{max}$ is between 2r and $\pi r$. The corresponding liposome size selected as liposome radius r in unit of $a_{lip}$, as plotted along y-axis. The selection of s relies on especially the lipid charge and other charge related properties of lipid monolayer (Ashrafuzzaman and Tuszynski, 2012). For simplicity, low order values of s for smaller aptamer length and smaller value of $q_{lip}$.

Example 4.8

Special Condition: Aptamer-Cell Interactions

The total energy of aptamer-cell association is:

$E_{net,Apt} = E_{HI}$ given ø=90° presumably negating $F_{SCI}$, so contribution from $E_{SCI}$ for aptamer getting dragged towards cell center is zero and there is no contribution of bending energies from either membrane or aptamer.

Example 4.9

Special Condition: Liposome-to-Cell Transition

Considering a constant value for $E_{HI}$, in aptamer-liposome interactions, the interplay between SCI interaction energy and the total bending energies of aptamer and lipid monolayer determines the aptamer length specific to liposome size by calculation of values of r' as in FIG. 5, where the values cross over the plateau for heading quickly to high energy values. These values of r', as $r'_{cut-off}^s$ determines the values of r in unit of $a_{lip}$ ($r'=r/a_{lip}$). s is screening order. For an aptamer with length of 2n nucleotides in a linear sequence the corresponding liposome size follows from the values of $r'_{cut-off}^s$ equal to $r'_{cut-off}^1$, $r'_{cut-off}^2$, $r'_{cut-off}^3$, $r'_{cut-off}^4$, ..., etc. ($r'_{cut-off}^1 < r'_{cut-off}^2 < r'_{cut-off}^3 < r'_{cut-off}^4 < ...$, etc.) for screening order 1, 2, 3, 4, ..., etc. Thus, depending on screening order, there can also be a distribution of liposome sizes for which a same aptamer may be effective. The distribution of liposome size depends perhaps mainly on $Q_r$, the relative charge of ABB to lipid. So the nucleotide arrangement and the lipid type of the liposome surface also influences the screening order, and therefore the liposome size distribution. That means for the same aptamer length, different nucleotide arrangements may also show different liposome binding energetics. The energetics are also affected by variation in lipid composition on liposome surface.

Example 5

In Vitro Aptamer-Liposome Binding: Case Study for Experimental Validation

Figure 6:
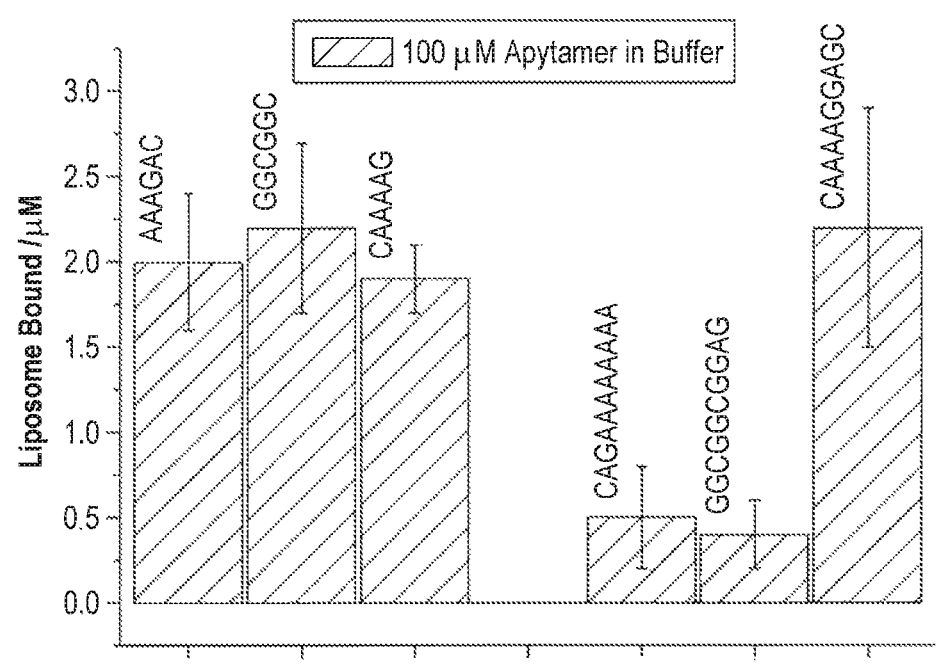
FIG. 6 shows exemplary aptamer binding to liposomes in vitro. Aptamers were chosen to have n=6 (aptamer short sequence; ASS) or 10 (aptamer long sequence; ALS) and designed to target either PS or PC designed according to the present method (SCI) or EFBA. The aptamers used were AAAGAC (PS/EFBA), GGCGGC (PS/SCI), CAAAAG (PC/SCI) and CAGAAAAAAAA (PS/EFBA) (SEQ ID NO.

FIG. 6 shows experimental aptamer binding to liposomes. AAAGAC (PS/EFBA), GGCGGC (PS/SCI), CAAAAG (PC/SCI) and CAGAAAAAAAA (PS/EFBA) (SEQ ID NO: 18), GGCGGCGGAG (PS/SCI) (SEQ ID NO: 1), CAAAAGGAGC (PC/SCI) (SEQ ID NO: 6) are ASS and ALS, respectively. 6 nucleotide short sequences (ASS) and 10 nucleotide (long sequences) were compared. Experiments were repeated in five independent conditions. Liposomes were constructed with following lipid molar ratios: PC:PS=10:1 (10% PS in liposome; used for testing PS aptamer binding, data shown here) and 10:0 (0% PS and 100% PC in liposome; used for testing both PC and PS aptamer binding, independently). Two control experiments were as follows: (i) Liposome bound value for PS or PC aptamer binding to liposomes having 0% aptamer (control from drug perspective) was 0.20±0.14 µM. (ii) Liposome bound value for PS aptamer binding to liposomes having 0% PS (control from target lipid perspective) was 0.27±0.18 µM. Triton X-100 and varied pH induced changes of physiological condition of liposome containing buffer influence the binding of aptamers to liposomes.

FIG. 6 demonstrates the amount of liposome bound aptamers detected by NanoDrop according to methods described in Ashrafuzzaman and Tseng, 2016. The liposomes were incubated with 100 µM aptamers in buffer. The liposome preparation and experimental techniques on aptamer detection in liposomes using NanoDrop are explained in Ashrafuzzaman and Tseng, 2016. PS aptamers designed using either EFBA or SCI to have short sequences bind better than long sequences. This behavior is not observed for aptamers designed for PC. This suggests that shorter PS aptamers easily bind or penetrate into the PS containing liposome having more negative curvature, e.g., more inter lipid space. For PC liposomes the lipid curvature is zero, so both shorter and longer types of aptamers may penetrate with equal potency.

It is to be understood that the PS and PC liposomes and related compositions and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for designing aptamers, the method comprising the steps of:

determining a target biomolecule and a spatial charge distribution of the target biomolecule;

constructing an aptamer from a series of aptamer building blocks to target the target biomolecule, the aptamer comprising RNA or DNA; the aptamer building blocks including a first aptamer building block for positioning nearest to the target molecule, the first aptamer build block comprising a lowest binding energy conformation level, a plurality of intermediate aptamer building blocks successively positioned after the first aptamer building block, the intermediate aptamer building blocks increasing in binding energy conformation level with increasing distance from the target biomolecule, and a last aptamer building block for positioning furthest from the target molecule, the last aptamer building block defining an aptamer-target binding energy saturation level; and synthesizing the aptamer containing the series of aptamer building blocks.

2. The method of claim 1, wherein the target biomolecule is selected from the group consisting of lipids, globular proteins, enzymes, amino acids, peptides, membrane proteins, DNA, and RNA.

3. The method of claim 2, wherein the target biomolecule is a lipid selected from the group consisting of phosphatidylcholine and phosphatidylserine.

4. The method of claim 3, wherein the lipid is phosphatidylserine.

5. The method of claim 4, wherein the binding energy conformation level is based on screened Coulomb interactions and the aptamer comprises SEQ ID NO: 1.

6. The method of claim 3, wherein the lipid is phosphatidylcholine and the aptamer comprises SEQ ID NO: 6.

7. The method of claim 3, wherein the lipid is embedded in the lipid membrane and the method further comprises:

determining a range of radii of curvature of the lipid membrane from $r_s$ to $r_L$;

choosing a range of predetermined aptamer lengths from 2 aptamers to less than or equal to $\pi r_L/a_{nu}$, where $a_{nu}$ is the average distance between each aptamer building block in the aptamer; and using each of the range of predetermined aptamer lengths to design an aptamer according to the method of claim 1.

8. A method for designing aptamers, the method the comprising steps of:

determining a spatial charge distribution of a target;

selecting a set of possible aptamer building blocks from which to design the aptamer;

selecting a first aptamer building block by calculating the zeroth order screened coulomb interaction term for each of the possible aptamer building blocks and selecting the possible aptamer building block corresponding to the maximal zeroth order screened coulomb interaction term to be the first aptamer building block;

selecting a subsequent aptamer building block selected from the set of possible aptamer building blocks by calculating the subsequent order screened coulomb interaction term for each of the aptamer building blocks and selecting the aptamer building block corresponding to the maximal subsequent order screened coulomb interaction term;

repeating the step of selecting a subsequent aptamer building block until the lowest subsequent order screened coulomb interaction term is less than an allowable minimal threshold or until a predetermined length of n aptamer building blocks is reached; and synthesizing the aptamer containing the series of aptamer building blocks.

9. The method of claim 8, wherein the target is embedded in a lipid membrane, the lipid membrane has a radius of curvature in a range from $r_s$ to $r_L$; wherein a predetermined aptamer length has a maximum length corresponding to a maximum order s selected by calculating $E_{net,Apt}-E_{HI}$ according to $\{(1/(K_B T))\}\{E_{net,Apt}-E_{HI}\}=Q_r^s \; \{[(q_{lip}^2/\varepsilon_0 \varepsilon_r)]^s/(k_B T)\}2\ \exp(2r'/n)+\{(½)\ (1/r_{Apt/lip})^2)\ (n^2+5)\}/r'^2$, taking the tangent lines at r=0 and as r approaches infinity, determining an intersection point and selecting the corresponding r as $r_{cutoff}$ for SCI orders from 0 to $s_{max}$, where $s_{max}$ corresponds to a $r_{cutoff}$ of approximately $r_L$; and truncated to be the length corresponding to $s_{max}$ or chosen to be the length corresponding to $s_{max}$, directly.

* * * * *

SEQUENCE LISTING

```
<160> NUMBER OF SEQ ID NOS: 17

<210> SEQ ID NO 1
<211> LENGTH: 10
<212> TYPE: DNA
<213> ORGANISM: Artificial Sequence
<220> FEATURE:
<223> OTHER INFORMATION: APTAMER

<400> SEQUENCE: 1
ggcggcggag                                                          10

<210> SEQ ID NO 2
<211> LENGTH: 10
<212> TYPE: DNA
<213> ORGANISM: Artificial Sequence
<220> FEATURE:
<223> OTHER INFORMATION: Aptamer

<400> SEQUENCE: 2
ggcggcggtg                                                          10

<210> SEQ ID NO 3
<211> LENGTH: 10
<212> TYPE: RNA
<213> ORGANISM: Artificial Sequence
<220> FEATURE:
<223> OTHER INFORMATION: APTAMER

<400> SEQUENCE: 3
ggcggcggug                                                          10

<210> SEQ ID NO 4
<211> LENGTH: 10
<212> TYPE: DNA
<213> ORGANISM: Artificial Sequence
<220> FEATURE:
<223> OTHER INFORMATION: APTAMER

<400> SEQUENCE: 4
ggcggcgaag                                                          10

<210> SEQ ID NO 5
<211> LENGTH: 10
<212> TYPE: DNA
<213> ORGANISM: Artificial Sequence
```

```
<220> FEATURE:
<223> OTHER INFORMATION: APTAMER

<400> SEQUENCE: 5
ggcggcggaa                                                                  10

<210> SEQ ID NO 6
<211> LENGTH: 10
<212> TYPE: DNA
<213> ORGANISM: Artificial Sequence
<220> FEATURE:
<223> OTHER INFORMATION: APTAMER

<400> SEQUENCE: 6
caaaaggagc                                                                  10

<210> SEQ ID NO 7
<211> LENGTH: 10
<212> TYPE: DNA
<213> ORGANISM: Artificial Sequence
<220> FEATURE:
<223> OTHER INFORMATION: APTAMER

<400> SEQUENCE: 7
gaaaaggagc                                                                  10

<210> SEQ ID NO 8
<211> LENGTH: 10
<212> TYPE: DNA
<213> ORGANISM: Artificial Sequence
<220> FEATURE:
<223> OTHER INFORMATION: APTAMER

<400> SEQUENCE: 8
caaaaggaga                                                                  10

<210> SEQ ID NO 9
<211> LENGTH: 10
<212> TYPE: DNA
<213> ORGANISM: Artificial Sequence
<220> FEATURE:
<223> OTHER INFORMATION: APTAMER

<400> SEQUENCE: 9
gaaaaggaga                                                                  10

<210> SEQ ID NO 10
<211> LENGTH: 10
<212> TYPE: DNA
<213> ORGANISM: Artificial Sequence
<220> FEATURE:
<223> OTHER INFORMATION: APTAMER

<400> SEQUENCE: 10
caaaaggatc                                                                  10

<210> SEQ ID NO 11
<211> LENGTH: 10
<212> TYPE: DNA
<213> ORGANISM: Artificial Sequence
<220> FEATURE:
<223> OTHER INFORMATION: APTAMER

<400> SEQUENCE: 11
gaaaaggatc                                                                  10
```

```
<210> SEQ ID NO 12
<211> LENGTH: 10
<212> TYPE: RNA
<213> ORGANISM: Artificial Sequence
<220> FEATURE:
<223> OTHER INFORMATION: APTAMER

<400> SEQUENCE: 12
caaaaggauc                                                                 10

<210> SEQ ID NO 13
<211> LENGTH: 10
<212> TYPE: RNA
<213> ORGANISM: Artificial Sequence
<220> FEATURE:
<223> OTHER INFORMATION: APTAMER

<400> SEQUENCE: 13
gaaaaggauc                                                                 10

<210> SEQ ID NO 14
<211> LENGTH: 10
<212> TYPE: DNA
<213> ORGANISM: Artificial Sequence
<220> FEATURE:
<223> OTHER INFORMATION: APTAMER

<400> SEQUENCE: 14
caaaaggata                                                                 10

<210> SEQ ID NO 15
<211> LENGTH: 10
<212> TYPE: DNA
<213> ORGANISM: Artificial Sequence
<220> FEATURE:
<223> OTHER INFORMATION: APTAMER

<400> SEQUENCE: 15
gaaaaggata                                                                 10

<210> SEQ ID NO 16
<211> LENGTH: 10
<212> TYPE: RNA
<213> ORGANISM: Artificial Sequence
<220> FEATURE:
<223> OTHER INFORMATION: APTAMER

<400> SEQUENCE: 16
caaaaggaua                                                                 10

<210> SEQ ID NO 17
<211> LENGTH: 10
<212> TYPE: RNA
<213> ORGANISM: Artificial Sequence
<220> FEATURE:
<223> OTHER INFORMATION: APTAMER

<400> SEQUENCE: 17
gaaaaggaua                                                                 10
```